United States Patent [19]
Gabriel

[11] 4,285,672
[45] Aug. 25, 1981

[54] MORTISE LOCK FOR LOCKING A REMOVABLE TOOTH-REPLACEMENT PROSTHESIS

[76] Inventor: Wolfgang Gabriel, Ostallee 17, 5500 Trier, Fed. Rep. of Germany

[21] Appl. No.: 135,161

[22] Filed: Mar. 28, 1980

[51] Int. Cl.³ .............................................. A61C 8/00
[52] U.S. Cl. .................................................. 433/172
[58] Field of Search ............... 433/172, 181, 182, 183, 433/204

[56] References Cited
U.S. PATENT DOCUMENTS

| | | | |
|---|---|---|---|
| 1,008,028 | 11/1911 | Gollobin et al. | 433/172 |
| 1,702,282 | 2/1929 | Stoloff | 433/172 |
| 4,085,506 | 4/1978 | Lew | 433/172 |

Primary Examiner—Robert Peshock
Attorney, Agent, or Firm—Robert W. Beach; Ward Brown; Douglas E. Winters

[57] ABSTRACT

An artificial tooth has embedded therein a mortise lock including a housing set into the tooth and accommodating a bolt member which is slidable to protrude from the interior of the housing to engage into a recess in a keeper which is fixed firmly to the jaw bone of a patient. The mortise lock includes an elastic ring which is movable with the bolt and engages a collar in the end of the housing when the lock is in unlocked position, to prevent the bolt from being removed from the housing. The collar is detachable to enable removal of the bolt for replacement of the elastic ring.

12 Claims, 4 Drawing Figures

MORTISE LOCK FOR LOCKING A REMOVABLE TOOTH-REPLACEMENT PROSTHESIS

BACKGROUND OF THE INVENTION

This invention relates to a mortise, (or plug-in) lock for locking a removable tooth replacement prosthesis with a part adapted to be firmly fixed in the jaw bone of a patient, the lock comprising a lock housing which is embedded in the tooth replacement prosthesis and in which a locking bolt is mounted so as to be displaceable so that one end thereof engages into a recess in a keeper fixed to the jaw bone.

Already known are various embodiments of mortise locks which serve to retain a removable tooth replacement prosthesis on a part of a tooth replacement assembly which is firmly fixed in the jaw bone. By operating such a mortise lock, the lock can be released, so that the tooth replacement prosthesis can be removed from the jaw.

The known mortise locks of this kind have the disadvantage that they have to be worked very precisely if the tooth replacement prosthesis is to be reliably fixed. An accurate snug fit, however, results in high frictional resistance, which impedes the mobility of the locking bolt and which, after fairly long use, abates as a result of wear.

In a particular known mortise lock (U.S. Pat. No. 1,008,028) the locking bolt is slotted, whereby its front end, which is insertable through a bridge into a tooth, is expanded and, upon the insertion of the locking bolt, is applied resiliently into its guide.

However, this mortise lock has the disadvantages that when the locking bolt is inserted, pressure is constantly exerted on the tooth into which it projects, and that the locking bolt can be withdrawn completely from its holder, whereby it can easily be lost. The object of the invention is, therefore, to provide a mortise lock suitable for locking a tooth prosthesis in place which even with frequent use ensures a good snug fit, without excessive precision work being necessary in producing the device.

The foregoing object is met in a mortise lock which includes a locking bolt having an encircling elastic collar which is movable with the bolt and is supported against the inner wall of the lock housing.

In an advantageous embodiment, the locking bolt has an encircling annular groove in which there is arranged a spring ring which projects at the curved surface of the bolt and abuts against the inner wall of the locking housing. This spring ring is preferably arranged releasably on the locking bolt.

In accordance with a preferred embodiment, the end face of the lock housing remote from the keeper, is connected releasably to the housing in which the locking bolt is displaceable. In the unlocked position, the inner surface of this end face is designed as a stop for the collar of the locking bolt.

In accordance with a further embodiment, arranged in the inner wall of the lock housing is an annular groove into which, in the locked position, the elastic collar or spring ring of the locking bolt engages.

The invention will be described further with reference to the accompanying drawings, in which.

Figure 1:
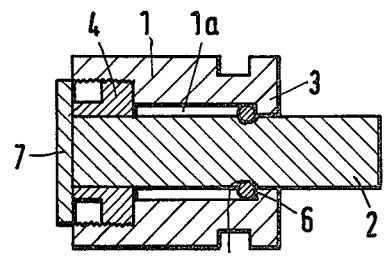
FIG. 1 is a sectional elevation of a preferred embodiment of the mortise lock of the invention, this being shown in the locking condition.
Figure 2:
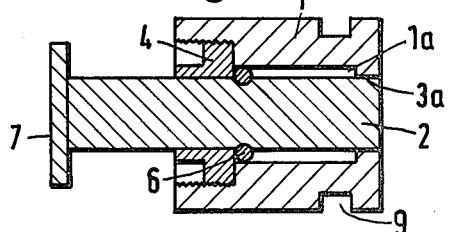
FIG. 2 is a view similar to FIG. 1 but showing the lock in its unlocked condition.
Figure 3:
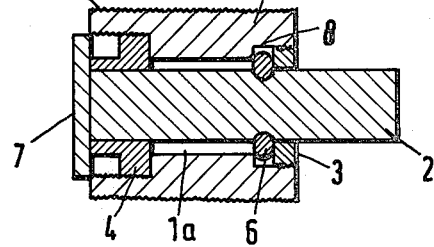
FIG. 3 is a view similar to FIG. 1, but showing a second embodiment of the mortise lock of the invention in its locking condition.

The mortise locks illustrated respectively in FIGS. 1 and 2 and in FIG. 3 comprise a lock housing 1 which includes a longitudinal cylindrical hollow interior space 1a in which a locking bolt 2 is displaceably accommodated. One end of lock housing 1 has an end wall 3 through which is an aperture 3a which corresponds to the cross-section of the locking bolt 2. The other end of the space 1a accommodates a collar 4 which is screwed into the lock housing 1 and also has therethrough an aperture which corresponds to the cross-section of the locking bolt 2.

The locking bolt 2 has, approximately in its middle, an encircling groove 5 in which an elastic or spring ring 6 is located. On one end of the locking bolt 2 is a stop disc 7.

As can be seen from FIGS. 1 and 3, in the locking position of the bolt 2, the spring ring 6 butts against the inner face of the end wall 3. Correspondingly, the stop disc 7 butts against the outside of the outer end of the collar 4, so that the locking bolt 2 cannot be further extended in the locking direction.

To unlock the mortise lock, the locking bolt 2 is displaced by use of the stop disc 7, until the position of FIG. 2 is reached. Then, the spring ring 6 lies against the inner face of the collar 4, and the locking bolt 2 no longer projects beyond the end wall 3 of the lock housing 1. During this displacement, only the spring ring 6 contacts the inner surface of the housing, whilst the locking bolt 2 itself does not contact the inner surface of the housing in any way. Since the spring ring 6 is elastic, a good snug fit is at all times ensured. Should the spring ring 6 become worn after frequent use, then it can be replaced by a new spring ring. For this purpose it is merely necessary to screw the collar 4 out of the lock housing 1, and then to withdraw the locking bolt 2 completely, whereupon the spring ring 6 can be taken out of the annular groove and a fresh ring can be put in its place.

Thus, the spring ring 6, on the one hand, serves the function of guiding the locking bolt 2 and, on the other hand, by abutment of the end face 4, serves to prevent unintentional withdrawal of the locking bolt.

In the embodiment of FIG. 3, the end wall 3 is a screwed-in ring in the lock housing 1. The end wall 3 and lock housing 1 create an annular groove 8 which allows the spring ring 6 to relax when the locking bolt 2 is in the locked position. The spring ring 6 then serves to retain the locking bolt 2 in the locked position and to prevent unintentional unlocking movement thereof.

Figure 4:
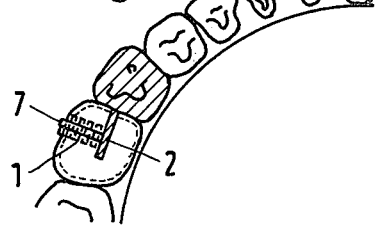
FIG. 4 illustrates, in plan, the mortise lock of FIGS. 1 and 2 operative to locate a tooth replacement prosthesis in position between adjacent teeth in a patient's mouth.

So that the lock housing 1 has a firm seat in the removable tooth replacement prosthesis, it is provided with roughening or knurling 9 on its outside. FIG. 4 shows the mortise lock in use. As can be seen, it is embedded in an artificial tooth which is slotted to receive a keeper in the form of a tongue or like part projecting from the patient's jaw bone or an adjacent natural tooth (shown shaded in the drawing). Locking of the artificial tooth in place is effected by moving the locking bolt 2 to its position of FIG. 1 or 3 to engage by its protruding end into the tongue or like part.

I claim:

1. In mechanism for locking a dental prosthesis to a keeper fixed in a patient's mouth, such mechanism including a housing adapted to be fixed in the prosthesis and a bolt having a portion received in the housing and slidable relative thereto between a locked position in which one end portion of the bolt projects from the housing for engagement with the keeper to lock the prosthesis in the patient's mouth and an unlocked position in which such bolt one end portion is retracted for disengagement from the keeper to free the prosthesis for removal from the patient's mouth, the improvement comprising the housing having a first end wall forming a flange projecting generally inward toward the bolt portion received in the housing, and an elastic ring encircling the bolt and moved therewith between the locked and unlocked positions of the bolt, said housing first end wall being abutted by said elastic ring in unlocked position of the bolt for limiting retraction of the bolt.

2. In the mechanism defined in claim 1, the housing first end wall being remote from the bolt first end portion, the housing having a second end wall adjacent to the bolt first end portion forming a flange projecting generally inward toward the bolt, and the housing second end wall being abutted by the elastic ring in locked position of the bolt for limiting projection of the bolt.

3. In the mechanism defined in claim 2, the housing second end wall being a collar releasably connected to the remainder of the housing.

4. In the mechanism defined in claim 1, the elastic ring being detachable from the bolt.

5. In the mechanism defined in claim 4, the housing first end wall being a collar releasably connected to the housing so that the housing first end wall is detachable from the remainder of the housing enabling removal of the bolt for replacement of the elastic ring.

6. In mechanism for locking a dental prosthesis to a keeper fixed in a patient's mouth, such mechanism including a housing adapted to be fixed in the prosthesis and a bolt having a portion received in the housing and slidable relative thereto between a locked position in which one end portion of the bolt projects from the housing for engagement with the keeper to lock the prosthesis in the patient's mouth and an unlocked position in which such bolt one end portion is retracted for disengagement from the keeper to free the prosthesis for removal from the patient's mouth, the improvement comprising the housing having a first end wall forming an annular flange projecting generally inward toward the bolt, the bolt portion received in the housing having a lateral projection intermediate said housing first end wall and such bolt one end portion which projectionis moved with the bolt between its locked and unlocked positions, said housing first end wall being abutted by said projection in unlocked position of the bolt for limiting retraction of the bolt, and said housing first end wall being a collar releasably connected to the housing so that said housing first end wall is detachable from the remainder of the housing enabling removal of the bolt.

7. In the mechanism defined in claim 6, the lateral projection being an elastic ring encircling the bolt and movable therewith but detachable therefrom.

8. In the mechanism defined in claim 1 or 7, the bolt having a circumferential groove receiving the elastic ring.

9. In the mechanism defined in claim 1 or 7, the elastic ring being engaged between the bolt and the inner periphery of the housing as the bolt is slid between its locked and unlocked positions for guiding movement of the bolt.

10. In the mechanism defined in claim 1 or 7, the inner periphery of the housing having a circumferential groove receiving the elastic ring in locked position of the bolt for retaining the bolt inlocked position.

11. In the mechanism defined in claim 5, 6 or 7, the collar and an end portion of the housing having complemental threads so that the collar is releasably connected to the housing by screw connection.

12. In the mechanism defined in claim 5, 6 or 7, the housing being embedded in the dental prosthesis with the collar forming the housing first end wall exposed for detachment from the remainder of the housing enabling removal of the bolt without separating the remainder of the housing from the dental prosthesis.

* * * * *